US010306923B2

(12) United States Patent
Kananen

(10) Patent No.: US 10,306,923 B2
(45) Date of Patent: Jun. 4, 2019

(54) APPARATUS AND METHOD FOR CONTROLLING ELECTRIC VAPORIZER

(71) Applicant: Pixan Oy, Oulunsalo (FI)

(72) Inventor: Mika Kananen, Oulunsalo (FI)

(73) Assignee: Pixan OY, Oulunsalo (FI)

( * ) Notice: Subject to any disclaimer, the term of this patent is extended or adjusted under 35 U.S.C. 154(b) by 148 days.

(21) Appl. No.: 14/911,851

(22) PCT Filed: Aug. 14, 2014

(86) PCT No.: PCT/FI2014/050624
§ 371 (c)(1),
(2) Date: Feb. 12, 2016

(87) PCT Pub. No.: WO2015/022448
PCT Pub. Date: Feb. 19, 2015

(65) Prior Publication Data
US 2016/0192706 A1  Jul. 7, 2016

(30) Foreign Application Priority Data
Aug. 14, 2013  (FI) ...................................... 20135829

(51) Int. Cl.
A61M 15/06 (2006.01)
A24F 47/00 (2006.01)
(Continued)

(52) U.S. Cl.
CPC ............ *A24F 47/008* (2013.01); *A24B 15/16* (2013.01); *A61M 11/042* (2014.02);
(Continued)

(58) Field of Classification Search
CPC ... A24F 47/008; A61M 11/042; A61M 15/06; A61M 2205/8206; A61M 2205/3368;
(Continued)

(56) References Cited

U.S. PATENT DOCUMENTS 5,372,148 A  12/1994  McCafferty
6,040,560 A   3/2000  Fleischhauer et al.
(Continued)

FOREIGN PATENT DOCUMENTS

CN  202760174 U   3/2013
EP    2399636 A1  12/2011
(Continued)

OTHER PUBLICATIONS

Resistance Temperature.*

(Continued)

*Primary Examiner* — Gregory A Anderson
*Assistant Examiner* — Victoria Murphy
(74) *Attorney, Agent, or Firm* — Berggren LLP

(57) ABSTRACT

The present invention introduces a method for controlling the power of an electric vaporizer, i.e. an electronic cigarette. In the method, the resistance of the heating unit of the vaporizer is measured. The system includes a controller and a memory, and the latter comprises a table where values of resistances and their corresponding default voltage or power values are stored. Additionally, minimum and maximum limit values of the voltages or powers may be stored. Based on the measured resistance, a suitable power or voltage value is determined. The power source is set to feed the heating element according to the selection. The user may however set the voltage or power input smaller or larger through the input means, comprising button(s) and a screen; despite the resistance value, but set limit values are not allowed to be exceeded.

15 Claims, 2 Drawing Sheets

Figure 1:
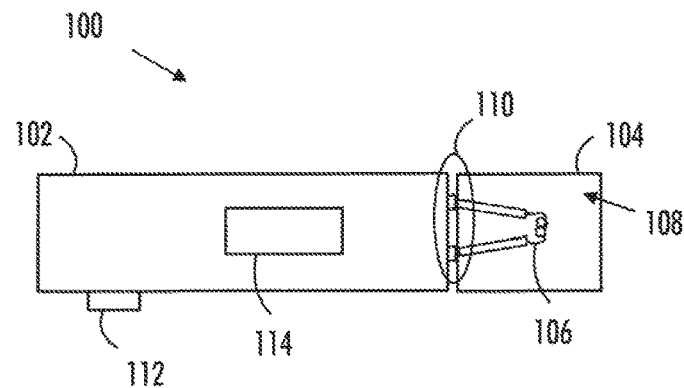

(51) Int. Cl.
*A24B 15/16* (2006.01)
*H05B 1/02* (2006.01)
*H05B 3/16* (2006.01)
*A61M 11/04* (2006.01)

(52) U.S. Cl.
CPC .......... *A61M 15/06* (2013.01); *H05B 1/0244* (2013.01); *H05B 3/16* (2013.01); *A61M 2205/3368* (2013.01); *A61M 2205/3653* (2013.01); *A61M 2205/8206* (2013.01); *H05B 2203/021* (2013.01); *H05B 2203/022* (2013.01)

(58) Field of Classification Search
CPC .............. A61M 2205/3653; H05B 3/16; H05B 1/0244; H05B 2203/022; H05B 2203/021; A24B 15/16
USPC .......................................... 219/497; 392/404
See application file for complete search history.

(56) References Cited

U.S. PATENT DOCUMENTS

| | | | |
|---|---|---|---|
| 2002/0079309 A1* | 6/2002 | Cox | A61M 11/041 219/486 |
| 2003/0226837 A1 | 12/2003 | Blake et al. | |
| 2010/0024816 A1 | 2/2010 | Weinstein et al. | |
| 2012/0174914 A1 | 7/2012 | Pirshafiey et al. | |
| 2013/0104916 A1 | 5/2013 | Bellinger et al. | |
| 2013/0199528 A1 | 8/2013 | Goodman et al. | |
| 2014/0334804 A1* | 11/2014 | Choi | A61M 15/06 392/404 |

FOREIGN PATENT DOCUMENTS

| | | |
|---|---|---|
| KR | 10-2010-0127817 A | 12/2010 |
| WO | 2013060781 A1 | 5/2013 |
| WO | 2013098398 A2 | 7/2013 |

OTHER PUBLICATIONS

Korean Intellectual Property Office, Notice to File a Response issued on KR appln. No. 10-2016-7006686, dated Dec. 23, 2016.
Korean Patent Office, Office action of South Korean Patent Application No. 2016-7006686, dated Aug. 4, 2016.
Finnish Patent and Registration Office search report for patent appln. No. FI20135829.
European Patent Office, Supplementary European Search Report issued on EP14836345.0, dated Mar. 28, 2017.
State Intellectual Property Office, P.R. China, First Office Action issued on 201480045426.7, dated Jan. 12, 2018.

* cited by examiner

APPARATUS AND METHOD FOR CONTROLLING ELECTRIC VAPORIZER

PRIORITY

This application is a national application of PCT application PCT/FI2014/050624, filed on Aug. 14, 2014 and claiming priority of the Finnish national application number FI20135829 filed on Aug. 14, 2013 and issued as FI125544 on Nov. 30, 2015, all of which are incorporated herein by reference in their entirety.

FIELD OF THE INVENTION

The invention relates generally to electronic vaporizers. Specifically the invention relates to controlling electric vaporizers.

BACKGROUND OF THE INVENTION

The following description of background art may include insights, discoveries, understandings or disclosures, or associations together with disclosures not known to the relevant art prior to the present invention but provided by the invention. Some such contributions of the invention may be specifically pointed out below, whereas other such contributions of the invention will be apparent from their context.

In recent year electronic vaporizers have been developed. One use for the vaporizers is to simulate smoking. The electronic vaporizers comprise a heating element configured to vaporize given material, typically liquid material, which is then inhaled by the user. The vaporizers comprise a power source for the heating element and some sort of controlling element for the vaporizing process.

The usage experience of electronic vaporizers depends on the components and the control process of the components of the vaporizer. The choice of the material to be inhaled is naturally important for the usage experience. Liquids with different flavours lead to different results. In addition, different types of heating elements and different power fed to the heating element have a strong effect on the usage experience. It has been noticed that best results are achieved when the power fed to the heating element is as constant as possible.

BRIEF DESCRIPTION

According to an aspect of the present invention, there is provided an apparatus as specified in claim 1.

According to another aspect of the present invention, there is provided a method as specified in claim 9.

LIST OF DRAWINGS

Figure 2:
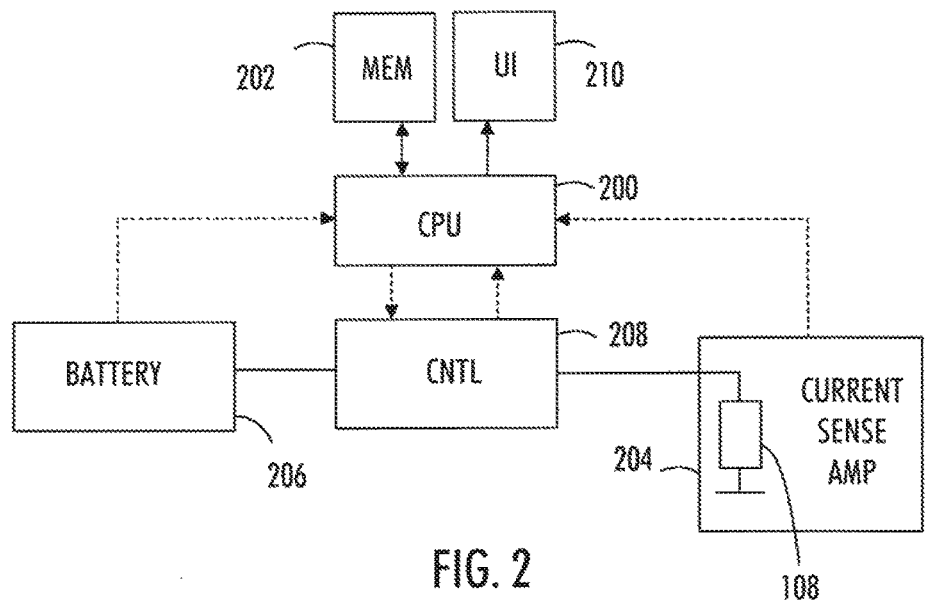
Figure 4:
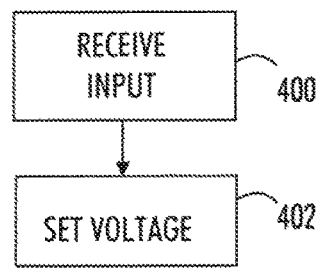
Figure 3:
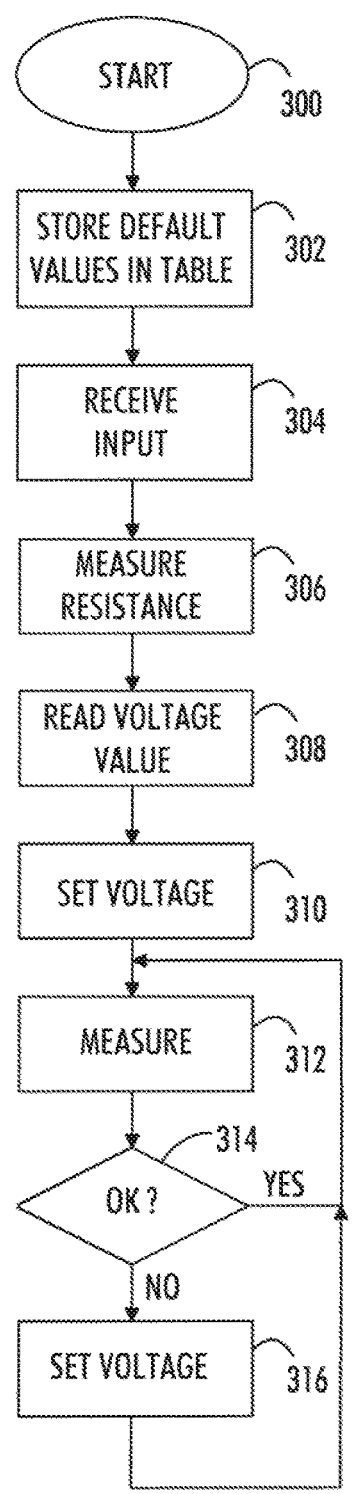

Embodiments of the present invention are described below, by way of example only, with reference to the accompanying drawings, in which FIG. 1 illustrates an example of an electric vaporizer;
FIG. 2 illustrates another example of an electric vaporizer;
FIGS. 3 and 4 are flow charts illustrating embodiments.

DESCRIPTION OF EMBODIMENTS

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Electric vaporizers are used for consuming or inhaling materials. Generally materials are in liquid which is heated by a heating element comprising a resistor. Electric power is fed to the heating element which vaporizes desired material for inhaling.

FIG. 1 illustrates an example of an electric vaporizer 100. The vaporizer 100 of FIG. 1 comprises a battery compartment 102 and a liquid compartment 104 comprising a heating element 106 and liquid 108 to be heated. Typically the liquid compartment 104 is detachable from the battery compartment 102. An electrical connection 110 connects the liquid compartment 104 and the battery compartment 102. The electric vaporizer 100 may comprise one or more buttons 112 and a display 114.

The user may change the liquid compartments 104 comprising a heating element 106. In addition, the heating element 106 of a liquid compartment 104 may be changed. The electrical properties of the heating elements may vary. For example if the heating element comprises a resistor wire, the electrical resistance of the resistor may vary. A typical value for the electrical resistance of a heating element varies between 0.3 to 10 ohms. The electrical resistance has an effect on the usage experience of the electronic vaporizer 100. There are devices on the market which let the user select a suitable power fed to the heating element when using the electronic vaporizer. However, these devices have some drawbacks. Typically the user is given a possibility to control the power over a given range. For example, the vaporizer may let the user to select a power between 5 to 15 watts. These solutions do not take the electrical properties of the heating element into account. Thus, it is possible for the user to select such a power which burns the heating element.

Let us study an example of the operation of the electric vaporizer in view of FIGS. 2 and 3. The embodiment starts at step 300. The electric vaporizer 100 comprises a controller 200 which controls the operation of the vaporizer. The vaporizer may comprise a memory 202 operationally connected to the controller 200. In some embodiments, the memory and the controller may be combined.

In step 302, the memory is configured to store a table comprising resistance values and a default power value for each resistance value. The power values may be predetermined on the basis of an experimental formula or empirical experiments, for example.

As illustrated in FIG. 1, the electric vaporizer 100 comprises a liquid compartment 104 comprising a heating element 106. Typically the liquid compartment 104 is detachable. The heating element 106 comprises a resistor wire. In an embodiment, the electric vaporizer comprises a current sense amplifier 204 connected to the heating unit 104. The electric vaporizer comprises a battery 206 which provides the electrical power required by the apparatus. The electric vaporizer may further comprise a power controller unit 208 which may be configured to control the power fed from the battery 206 to the heating unit 104 and the current sense amplifier 204. The power controller unit 208 may operate under the control of the controller 200. In an embodiment, the power controller unit 208 is realized as a buck-boost controller. A buck-boost controller is configured to control the power fed to a load to be either smaller or greater than the power given by a source battery.

Regarding the reference numberings in FIG. 1, the heating unit 104 is in practice the same as the liquid compartment.

The heating unit 104 thus comprises the heating element 106 and liquid 108 to be heated and vaporized for the user to inhale.

The electric vaporizer 100 further comprises user interface 210 which may be realized with one or more buttons and a display, for example. In an embodiment, a button may be reserved for initializing vaporizing operation. In an embodiment, some other buttons may be used for controlling the vaporizing operation. The button may be realized with push buttons, touch pad or with any other technology available.

In step 304, the controller is configured to receive input from the user via the user interface 210. The input may be a command to initialize vaporizing operation.

In step 306, the controller is configured to measure the resistance of the heating unit 104. The measurement may be performed by giving a command to the power controller unit and the current sense amplifier. The controller 200 may configure the power controller 208 to output a given voltage to the heating unit. The current sense amplifier may measure the current (and also the voltage) and send measurements to the controller. The controller may calculate the resistance of the heating unit using formula $R=U/I$, where U is voltage and I current.

In step 308, the controller is configured to read from the memory 202 a default voltage value corresponding to the determined resistance.

The use of a default value enables the protection of the heating unit. The heating unit cannot be damaged accidentally. In known solutions, when a heating unit requiring a large voltage is changed to a unit requiring small voltage, the changed unit may accidentally receive too large voltage and get damaged. In addition, the use of tested default values provides immediately a satisfactory user experience to the user.

One advantage related to the structure of the present electronic vaporizer is that the use of a power controller enables the use of a large range of voltages or powers which can be fed to the heating unit.

In step 310, the controller is configured to give a command to the power controller unit 208 to feed the default voltage value to the heating unit.

In an embodiment, the controller may be configured to measure the power fed to the heating unit 104, compare the measured power to the determined power, and control the power source on the basis of the comparison. In step 312, the measurement is performed by the current sense amplifier. The controller may compare the measurement to the required value in step 314 and correct the voltage in step 316 if needed. This procedure may be executed at given intervals or a few times after the initialization of the vaporizing procedure.

In an embodiment, the user may manually adjust the power fed to the heating unit using the user interface 210. For example, the user may be given the possibility of adjusting the voltage fed into the heating unit in steps of 0.1 volts. FIG. 4 illustrates this example. In step 400, the controller 200 detects that the user has indicated voltage up function. This may be realized with a power up button, for example. In step 402, the controller instructs the power control unit to increase the voltage fed to the heating unit by 0.1 volts. There may be some minimum and maximum values which the user is not allowed to exceed.

TABLE 1

| Resistance | Min limit | Default | Max limit |
|---|---|---|---|
| 0.5 | 1.9 | 2.3 | 2.7 |
| 0.6 | 2.0 | 2.6 | 3.0 |
| 0.7 | 2.4 | 3.0 | 3.5 |
| ... | ... | ... | ... |
| 5.4 | 5.9 | 7.4 | 8.7 |
| 5.5 | 6.2 | 7.8 | 9.0 |

Table 1 illustrates an example of data stored in the memory 202. The memory may store resistance values and corresponding default voltage or power values. In addition, for each resistance value a minimum and maximum value for the voltage or power may be stored.

The memory 202 may also store the current measured resistance value. If the same heating unit is used, the power or voltage values selected by the user may be used repeatedly. However, if the heating unit is changed such that the resistance changes, the controller 200 may detect the change and select the default power or voltage value for the determined resistance.

In an embodiment, the user is given the possibility to freely select any voltage or power value from a predetermined range, such as 2 to 8.2 volts, for example. In this mode, the resistance value measured from the heating unit has no effect.

The controller 200 may be implemented as an electronic digital computer, which may comprise a working memory (RAM), a central processing unit (CPU), and a system clock. The CPU may comprise a set of registers, an arithmetic logic unit, and a control unit. The control unit is controlled by a sequence of program instructions transferred to the CPU from the RAM. The control unit may contain a number of microinstructions for basic operations. The implementation of microinstructions may vary, depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

It will be obvious to a person skilled in the art that, as technology advances, the inventive concept can be implemented in various ways. The invention and its embodiments are not limited to the examples described above but may vary within the scope of the claims.

The invention claimed is:

1. A controller of an electronic vaporizer, wherein the controller is configured to:
   store a table comprising resistance values and a corresponding power value for each resistance value;
   measure a resistance of a heating element of a heating unit of the electronic vaporizer;
   determine a power value for the measured resistance on the basis of the stored table, wherein a power value change in the stored table is disproportional to a corresponding change of the measured resistance; and
   control a power source to feed the heating element of the heating unit with the determined power value,
   wherein the determined power value fed to the heating unit is further adjustable by a user to be below a given maximum power and above a given minimum non-zero power from the stored table for the measured resistance value, where the determined power value is between the given maximum power and the given minimum non-zero power.

2. The controller of claim 1, wherein the controller is further configured to determine the resistance of the heating element at given time intervals and adjust a power fed to the heating element if the resistance changes.

3. The controller of claim 1, wherein the controller is further configured to prevent the feeding of the heating unit with a power if the measured resistance is outside of a given range.

4. The controller of claim 1, wherein the controller is further configured to detect an input of a user and measure the resistance of the heating element after the detection.

5. The controller of claim 1, wherein the controller is further configured to measure a power fed to the heating-element, compare the measured power to the determined power, and control the power source on the basis of the comparison.

6. The controller of claim 1, wherein the controller is further configured to control the power source to decrease or increase a power fed to the heating unit on the basis of an input from a user.

7. An electronic vaporizer comprising a controller which is configured to:
    store a table comprising resistance values and a corresponding power value for each resistance value;
    measure a resistance of a heating element of a heating unit of the electronic vaporizer;
    determine a power value for the measured resistance on the basis of the stored table, wherein a power value change in the stored table is disproportional to a corresponding change of the measured resistance; and
    control a power source to feed the heating element of the heating unit with the determined power value,
    wherein the determined power value fed to the heating unit is further adjustable by a user to be below a given maximum power and above a given minimum non-zero power from the stored table for the measured resistance value, where the determined power value is between the given maximum power and the given minimum non-zero power.

8. A method for controlling an electronic vaporizer using a controller, the method comprises:
    storing a table comprising resistance values and a corresponding power value for each resistance value;
    measuring a resistance of a heating element of a heating unit of the electronic vaporizer;
    determining a power value for the measured resistance on the basis of the stored table, wherein a power value change in the stored table is disproportional to a corresponding change of the measured resistance; and
    controlling a power source to feed the heating element of the heating unit with the determined power value,
    wherein the determined power value fed to the heating unit is further adjustable by a user to be below a given maximum power and above a given minimum non-zero power from the stored table for the measured resistance value, where the determined power value is between the given maximum power and the given minimum non-zero power.

9. The method of claim 8, further comprising: determining the resistance of the heating element at given time intervals and adjusting a power fed to the heating element if the resistance changes.

10. The method of claim 8, further comprising: preventing the feeding of the heating unit with a power if the measured resistance is outside a given range.

11. The method of claim 8, further comprising: detecting an input of a user and measuring the resistance of the heating element after the detection.

12. The method of claim 8, further comprising: measuring a power fed to the heating element, comparing the measured power to the determined power, and controlling the power source on the basis of the comparison.

13. The controller of claim 1, wherein the heating unit is replaceable with a further heating unit comprising a further heating element having a further resistance which is different than the resistance of the heating element wherein the controller is operable using the further heating unit.

14. The electronic vaporizer of claim 7, wherein the heating unit is replaceable with a further heating unit comprising a further heating element having a further resistance which is different than the resistance of the heating element, wherein the controller is operable using the further heating unit.

15. The method of claim 8, wherein the heating unit is replaceable with a further heating unit comprising a further heating element having a further resistance which is different than the resistance of the heating element, wherein the controller is operable using the further heating unit.

* * * * *